(12) United States Patent
Fukuda

(10) Patent No.: US 8,742,351 B2
(45) Date of Patent: Jun. 3, 2014

(54) SPECTROPHOTOMETER

(75) Inventor: Hisato Fukuda, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 313 days.

(21) Appl. No.: 13/132,064

(22) PCT Filed: Dec. 2, 2008

(86) PCT No.: PCT/JP2008/003560
§ 371 (c)(1),
(2), (4) Date: May 31, 2011

(87) PCT Pub. No.: WO2010/064276
PCT Pub. Date: Jun. 10, 2010

(65) Prior Publication Data
US 2011/0235034 A1    Sep. 29, 2011

(51) Int. Cl.
*G01J 3/42* (2006.01)
(52) U.S. Cl.
USPC ............. 250/338.1; 250/339.07; 250/339.08; 250/339.09; 356/319; 356/451; 356/456
(58) Field of Classification Search
USPC .................................................. 250/339.07
See application file for complete search history.

(56) References Cited

U.S. PATENT DOCUMENTS

| | | | |
|---|---|---|---|
| 4,766,551 A * | 8/1988 | Begley | 702/28 |
| 5,784,162 A * | 7/1998 | Cabib et al. | 356/456 |
| 6,714,304 B2 | 3/2004 | Ota | |
| 7,869,050 B2 * | 1/2011 | He et al. | 356/451 |
| 2003/0007155 A1 * | 1/2003 | Ota | 356/451 |
| 2003/0175843 A1 * | 9/2003 | Yamaguchi et al. | 435/22 |
| 2009/0296097 A1 * | 12/2009 | He et al. | 356/451 |

FOREIGN PATENT DOCUMENTS

| | | |
|---|---|---|
| JP | 58-201049 | 11/1983 |
| JP | 09159671 A | 6/1997 |
| JP | 10-123047 | 5/1998 |
| JP | 2002-022536 | 1/2002 |

(Continued)

OTHER PUBLICATIONS

International Preliminary Report on Patentability dated Jul. 5, 2011 and its English language translation for International application PCT/JP2008/003560.

(Continued)

*Primary Examiner* — David Porta
*Assistant Examiner* — Djura Malevic
(74) *Attorney, Agent, or Firm* — Bingham McCutchen LLP

(57) ABSTRACT

When a system is powered on and becomes ready for a measurement, it automatically begins to acquire an interferogram (IFG). When a new IFG is acquired, if a background (BKG) IFG is present in a memory but there is no sample IFG (S2 and S4), the new IFG is compared with the BKG-IFG and, if the two IFGs are identical, the new IFG is added to the BKG-IFG (S5, S6 and S7). When an operator sets a sample in a sample chamber and the new IFG shows a change, the IFG is stored as a sample IFG (S8). Then, a sample measurement is initiated. After that, when a new IFG is found to be identical to the sample IFG stored in the memory (S9 and S10), the new IFG is added to the sample IFG (S13). The sample measurement is completed when the number of sample IFGs stored in the memory has reached a predetermined accumulation number. Thus, the sample measurement is automatically performed, for which the operator only needs to set a sample. The workload on the operator is reduced and the measurement task can be efficiently performed.

6 Claims, 3 Drawing Sheets

(56) References Cited

FOREIGN PATENT DOCUMENTS

| | | |
|---|---|---|
| JP | 2002-509605 | 3/2002 |
| JP | 2003-014543 | 1/2003 |
| JP | 2004121214 A | 4/2004 |
| JP | 2007-078370 | 3/2007 |
| JP | 2008-275326 | 11/2008 |

OTHER PUBLICATIONS

Japanese language office action dated Jun. 5, 2012 and its English language translation issued in corresponding Japanese application 2010541144 cites the foreign patent documents above.

* cited by examiner

US 8,742,351 B2

SPECTROPHOTOMETER

CROSS-REFERENCE TO THE RELATED APPLICATIONS

The present application is a national stage of international application No. PCT/JP2008/003560 filed on Dec. 2, 2008, the entire contents of which are incorporated herein by reference.

TECHNICAL FIELD

The present invention relates to a spectrophotometer, and more specifically to a spectrophotometer in which a background measurement with no sample is performed using the same optical system as used in an actual measurement of the sample.

BACKGROUND ART

In a Fourier transform infrared spectrophotometer (hereinafter simply referred to as the "FTIR"), which is one type of spectrophotometer, an interfering light whose amplitude temporally changes is produced by a Michelson interferometer including a fixed mirror and a moving mirror. This light is thrown onto a sample, and a transmitted light or reflected light is detected as an interferogram. The interferogram is subjected to Fourier transformation to obtain an absorption spectrum with the horizontal axis representing the wave number and the vertical axis representing the intensity of light (e.g. absorbance or transmittance).

In the FTIR, which uses infrared light, absorption peaks due to unwanted components (e.g. water vapor or carbon dioxide) existing in the measurement optical path overlap the absorption peaks due to proper sample. Given this problem, an absorption spectrum with no sample is first obtained using the same measurement optical system as used in an actual measurement of the sample, and then this absorption spectrum (i.e. the background spectrum) is subtracted from an absorption spectrum obtained by an actual measurement with the sample set in the system, to obtain an absorption spectrum that reflects the true absorption by the sample (Patent Documents 1 and 2). Accordingly, in the transmission measurement using the FTIR, it is necessary to successively perform the three steps of performing a background measurement with no sample (this measurement is often called a "blank measurement" since no sample is set in the system), setting a sample in a sample chamber, and performing an actual measurement of the sample. The background measurement may be performed after the actual measurement of the sample, in which case the process of removing the sample from the sample chamber is required.

The recently used FTIRs are normally composed of an FTIR main unit for performing a measurement on a sample to collect data and a personal computer in which device-controlling and data-processing software programs for controlling the main unit and processing the collected data are installed. (This computer is hereinafter referred to as a "control PC.") To perform a background measurement or a sample measurement using this type of FTIR, an operator needs to perform an operation for performing the measurement by using a keyboard or a pointing device of the control PC. On the other hand, when setting a sample, the operator needs to set it at a proper position within the sample chamber of the FTIR main unit, using a holder, cell or similar device depending on the kind of the sample (e.g. solid, liquid, powder or thin film). If the FTIR main unit is placed remotely from the control PC for the convenience of system installation, the aforementioned three-stage process requires the operator to move from the control PC to the FTIR main unit and then back to the control PC. This is a troublesome and inefficient task.

FTIRs can obtain an absorption spectrum over a predetermined wavelength range through one cycle of the reciprocal movement of the moving mirror. However, the S/N ratio achieved by a single-cycle measurement is rather low. Therefore, in general, the reciprocal movement of the moving mirror is repeated many times to accumulate multiple sets of data of collected interferograms, and then subject the accumulated data to Fourier transformation to create an absorption spectrum with a high S/N ratio. Due to such a process, the measurement requires a considerable length of time. In order to perform the aforementioned three processes without wasting time between processes, it is desirable for an operator to stand by the FTIR main unit and wait for the completion of, for example, the background measurement. However, this significantly lowers the work efficiency since, as just explained, this measurement requires a considerable length of time.

Patent Document 1: JP-A 2002-22536
Patent Document 2: JP-A 2008-275326

DISCLOSURE OF THE INVENTION

Problems to be Solved by the Invention

The present invention has been developed to solve the previously described problems, and its primary objective is to provide a spectrophotometer with which an operator can efficiently perform the measurement task without repeatedly moving from the main unit to the control PC and vice versa. Another objective of the present invention is to provide a spectrophotometer capable of efficiently performing a measurement without using unnecessary time for the background measurement.

Means for Solving the Problems

The present invention aimed at solving the aforementioned problems is a spectrophotometer for throwing measurement light onto a sample, for detecting transmitted light from the sample by means of a detector, and for obtaining information relating to absorption of light at a specific wavelength by the sample based on detection data, including:

a) a recognizing means for obtaining the detection data continuously or at predetermined intervals of time, and for recognizing that a sample to be analyzed is set in an optical path judging from a degree of a temporal change in the detection data; and b) a processing means for initiating, in response to a recognition by the recognizing means, a process in which the detection data are treated as measurement data for the sample.

The spectrophotometer according to the invention begins to throw measurement light, for example, when the system is powered on, or when a predetermined command is given after the system is powered on. When no sample is set at a predetermined sample-setting position (e.g. a sample-setting position within a sample chamber), the measurement light directly reaches the detector without undergoing absorption by the sample. Meanwhile, an operator prepares a sample to be analyzed and places it at the designated sample-setting position in the measurement optical path. After this point in time, the measurement light passes through the sample, while undergoing absorption by the sample, before it reaches the detector. Accordingly, the detection data shows some change before and after the sample is set. The recognizing means recognizes this change and determines that a sample has been set. In response to this recognition, the processing means begins to treat the detection data as the measurement data which reflect the absorption by the sample. Thus, in the spectrophotometer according to the present invention, when an operator sets a sample at a designated sample-setting position, the system automatically begins to collect measurement data for a sample without any key operation or button operation for initiating the measurement.

In one preferable mode of the spectrophotometer according to the present invention, the processing means is configured so that, after the processing means begins to treat the detection data as the measurement data in response to the recognition by the recognizing means, when newly obtained detection data is found to be significantly different from the measurement data, the processing means discards this measurement data.

In the case where the operator opens an air-tight sample chamber, for example, and sets a sample in the chamber, the detection data changes after the sample is set. However, the detection data may possibly remain unstable until the ambience within the sample chamber or other conditions become stable. Given this problem, the spectrophotometer of the previously described mode is configured so that no detection data is actually treated as the measurement data while the detection data remain unstable, but detection data after becoming stable is adopted as proper measurement data. Thus, the reliability of the measurement data is enhanced.

As already explained, it is possible to consider that detection data with no sample is obtained until the recognizing means determines that a sample has been set. Accordingly, in the spectrophotometer according to the present invention, the processing means may perform a process in which the detection data obtained before the recognizing means recognizes the presence of the sample to be analyzed is treated as background data with no sample. The background data contain information about absorption or other influences due to unwanted components present in the air (or other kind of gas, such as purge gas) in the measurement optical path other than the sample. By using the measurement data obtained with a sample set in the system and the background data obtained with no sample, it is possible to remove the influences of unwanted components and other factors and calculate a correct absorption due to the sample.

The spectrophotometer according to the present invention can be effectively used in any case where the optical path for the background measurement is the same as the optical path for the actual measurement of the sample. Accordingly, there is basically no limitation on the measurement wavelength and the present invention can be generally applied to ultraviolet-visible spectrophotometers, infrared spectrophotometers and near-infrared spectrophotometers.

In the case of Fourier transform infrared spectrophotometers, which normally require a considerable length of time for the measurement, the automatic execution of the background measurement after the power-on of the system is particularly useful to reduce the workload on the operator and improve the efficiency of the measurement task. Though, in the Fourier transform infrared spectrophotometer, it is possible to recognize the setting of a sample in the measurement optical path based on the degree of change in the data after Fourier transformation, Fourier transformation process requires a considerable length of time. Furthermore, the Fourier transformation process puts heavy load on the arithmetic circuit. Therefore, when the spectrophotometer according to the present invention is a Fourier transform infrared spectrophotometer, it is preferable to configure the recognizing means so that the presence of the sample to be analyzed is recognized from a temporal change in an interference-waveform data obtained before the Fourier transformation.

Effects of the Invention

The spectrophotometer according to the present invention automatically begins to collect measurement data for a sample without requiring any special operation for initiating the sample measurement; the operator needs only to set the sample at a designated sample-setting position. Even if the main unit for performing the measurement is placed remotely from the personal computer having an operation unit for entering a command for initiating the measurement, the operator does not need to go to the operation unit and enter the measurement-initiating command after setting the sample. Thus, the workload on the operator is reduced and the efficiency of the measurement task is enhanced.

Furthermore, in the case where the spectrophotometer according to the present invention is configured so that the data collection process is automatically initiated after the system is powered on, it is unnecessary to perform an operation for initiating the background measurement with no sample set in the system. The operator does not need to stand by the main unit throughout the period of time from the initiation of the background measurement to the completion of this measurement. Therefore, the efficiency of the measurement task is further improved.

EXPLANATION OF NUMERALS

1 . . . Main Unit
10 . . . Interference Chamber
11 . . . Infrared Light Source
12 . . . Converging Mirror
13 . . . Collimating Mirror
14 . . . Beam Splitter
15 . . . Fixed Mirror
16 . . . Moving Mirror
20 . . . Parabolic Mirror
21 . . . Sample Chamber
22 . . . Sample
23 . . . Ellipsoidal Mirror
24 . . . Infrared Photodetector
25 . . . Amplifier
26 . . . A/D Converter
3 . . . Personal Computer (PC)
30 . . . Data Processor
31 . . . Data Bus
32 . . . New IFG Temporary Memory
33 . . . Sample IFG Accumulation Memory
34 . . . BKG-IFG Accumulation Memory
35 . . . R/W Controller
36 . . . New IFG Determination Processor 37 ... Accumulation Processor
40 ... Controller
41 ... Operation Unit
42 ... Display Unit

BEST MODE FOR CARRYING OUT THE INVENTION

An FTIR as one embodiment of the spectrophotometer according to the present invention is hereinafter described with reference to FIGS. 1-4.

Figure 1:
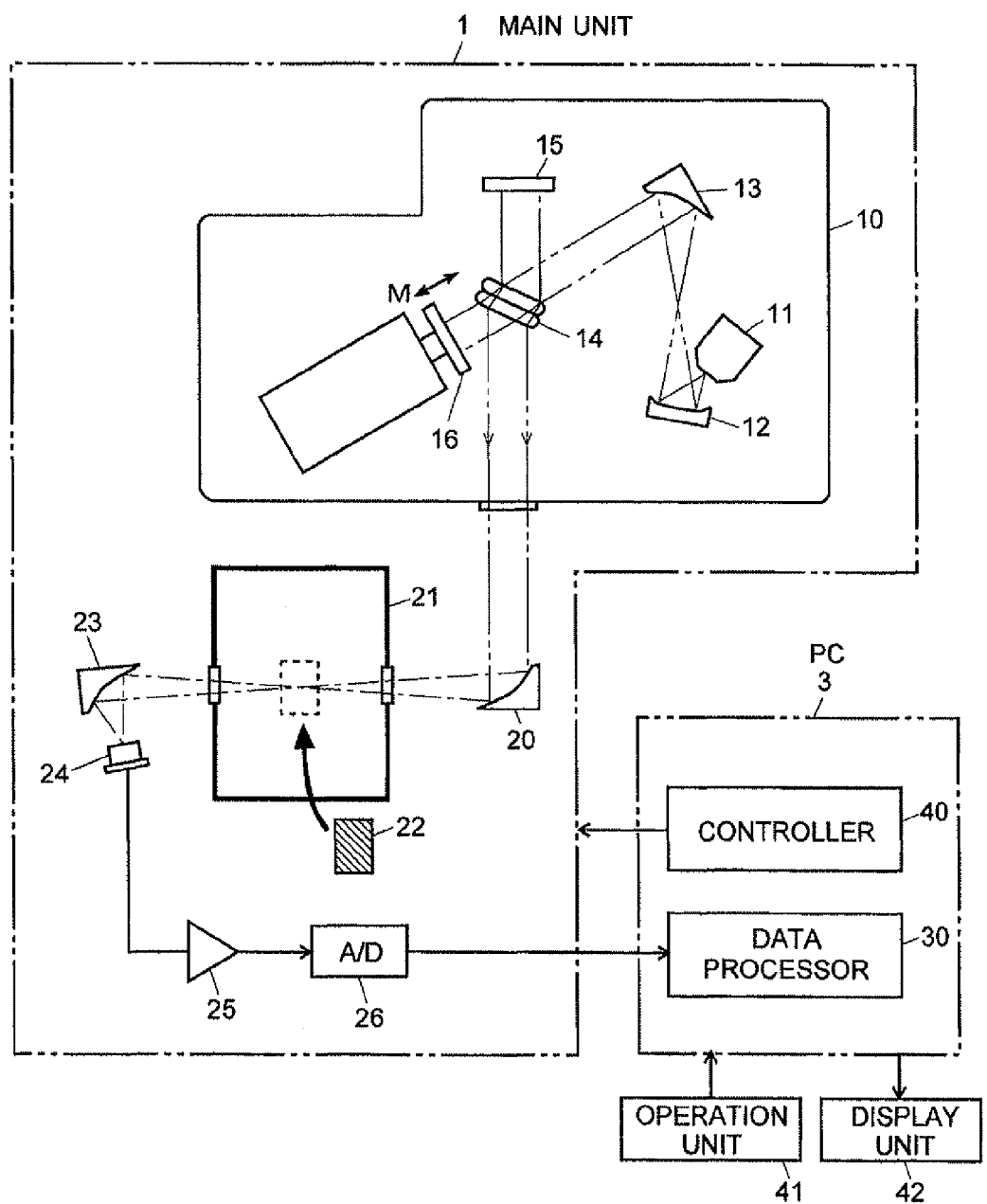
FIG. 1 is an overall configuration diagram of an FTIR as one embodiment of the spectrophotometer according to the present invention.

FIG. 1 is an overall configuration diagram of the FTIR of the present embodiment. The FTIR of the present embodiment consists of a main unit 1 for collecting data and a personal computer (PC) 3 in which control software programs for analyzing data and managing the overall control of the main unit 1 are installed. Depending on the design of system installation, the main unit 1 and the PC 3 may be placed next to each other or remotely from each other.

An interference chamber 10 is an air-tight container, which contains a Michelson interferometer consisting of an infrared light source 11, a converging mirror 12, a collimating mirror 13, a beam splitter 14, a fixed mirror 15, a moving mirror 16 and other elements. In this interferometer, a beam of infrared light emitted from the infrared light source 11 is thrown onto the beam splitter 14 via the converging mirror 12 and the collimating mirror 13. The beam splitter 14 separates that beam into two optical paths, one of which leads to the fixed mirror 15 and the other to the moving mirror 16. After being reflected by the fixed mirror 15 and the moving mirror 16, the two beams are merged back into one composite beam by the beam splitter 14 and exit from the interference chamber 10, to be sent to a parabolic mirror 20. During this process, the moving mirror 16 is reciprocally moving in the direction indicated by arrow M in FIG. 1. Accordingly, the composite beam produced by the beam splitter 14 becomes an interfering light (interferogram) whose amplitude temporally changes. The humidity in the interference chamber 10 is controlled to protect the beam splitter 14, which includes a substrate made of a deliquescent material, KBr, and for other purposes.

The interfering light converged by the parabolic mirror 20 is thrown into the sample chamber 21. If a sample 22 to be analyzed is set at a designated position in the sample chamber 21, the interfering light impinges on the sample 22, and the transmitted light is converged by the ellipsoidal mirror 23 and introduced into the infrared photodetector 24. If no sample 22 is set in the sample chamber 21, the interfering light is directly introduced into the infrared photodetector 24 without undergoing absorption by the sample 22. The light reception signal obtained with the infrared photodetector 24 is amplified by the amplifier 25 and introduced into the analogue-to-digital (A/D) converter 26, which converts the signal into data representing the interference waveform in a digitized form.

Though not shown in FIG. 1, a control interferometer, which generates an interfering laser beam for obtaining an interference fringe signal, is normally provided in the interference chamber 10. Based on the laser interference fringe signal obtained with a laser detector, a pulse signal for sampling the detection signal corresponding to the interfering infrared light with the A/D converter 26 is generated.

The data representing the interferogram are sent from the main unit 1 to the PC 3. In PC 3, the data are inputted into a data processor 30, which is a functional block realized by running the control software program. The data processor 30 creates an absorption spectrum for the sample by processing the input data in a manner to be described later and then performing a Fourier transform operation. The PC 3 further includes a controller 40, which sends various kinds of control signals to the main unit 1 according to the instructions or settings given through an operation unit 41, such as a keyboard or a pointing device (e.g. a mouse). A display unit 42 is also connected to the PC 3, on which a measurement result or other information can be displayed.

Figure 2:
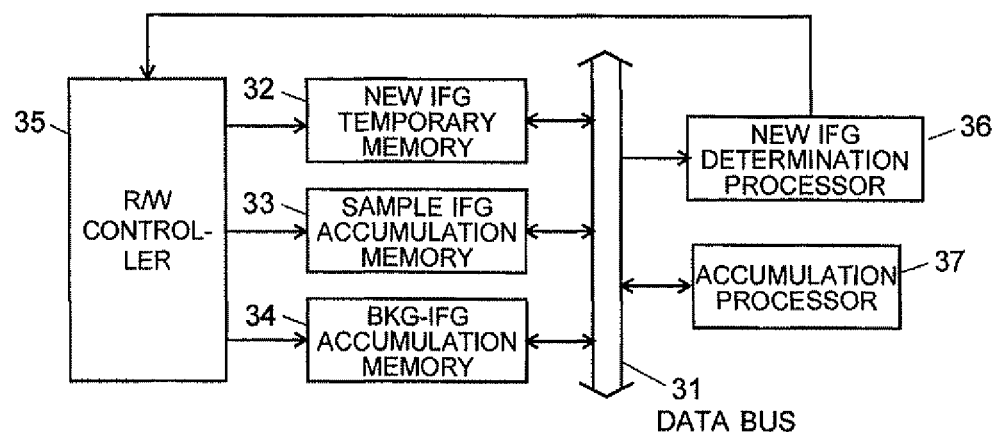
FIG. 2 is a functional block diagram showing the main components of the data processing unit in the FTIR of the present embodiment.

FIG. 2 is a functional block diagram showing the main components of the data processor 30. The data processor 30 includes a new IFG temporary memory 32, a sample IFG accumulation memory 33, a BKG-IFG accumulation memory 34, a new IFG determination processor 36, and an accumulation processor 37, which are all connected to a data bus 31, which in turn is connected to the output of the A/D converter 26 shown in FIG. 1. An R/W controller 35 is also provided. According to a result obtained by the new IFG determination processor 36, the R/W controller 35 reads data from the new IFG temporary memory 32 and newly or additionally stores the read data in either the sample IFG accumulation memory 33 or the BKG-IFG accumulation memory 34. In the present embodiment, the new IFG determination processor 36 corresponds to the recognizing means in the present invention and the R/W controller 35 corresponds to the processing means.

The new IFG temporary memory 32 has the capacity required for holding the data of an interferogram obtained by one cycle of the reciprocal motion of the moving mirror 16. The number of data is typically within a range from 1,000 to 10,000. On the other hand, the sample IFG accumulation memory 33 and the BKG-IFG accumulation memory 34 each have a capacity for holding data of n cycles of accumulation. For example, if the number of data forming one interferogram is 1,000, the two memories each have a capacity for holding 1,000×n pieces of data. The memories 32-34 do not need to be physically separated from each other; it is naturally possible to realize these memories by using different memory areas in the same memory device.

Figure 3:
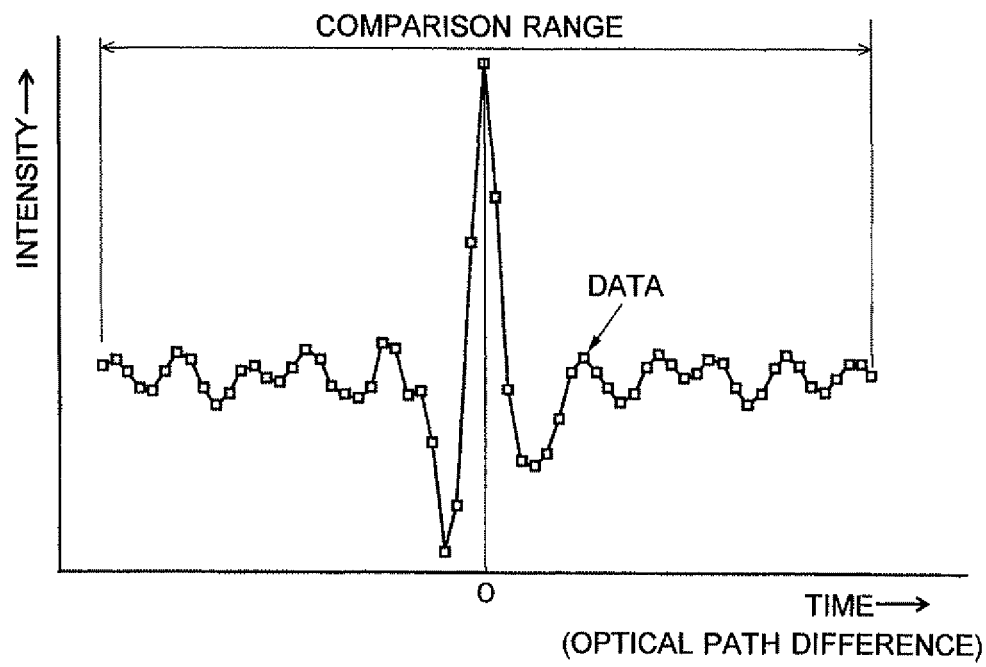
FIG. 3 is a waveform diagram for explaining an operation of the FTIR of the present embodiment.
Figure 4:
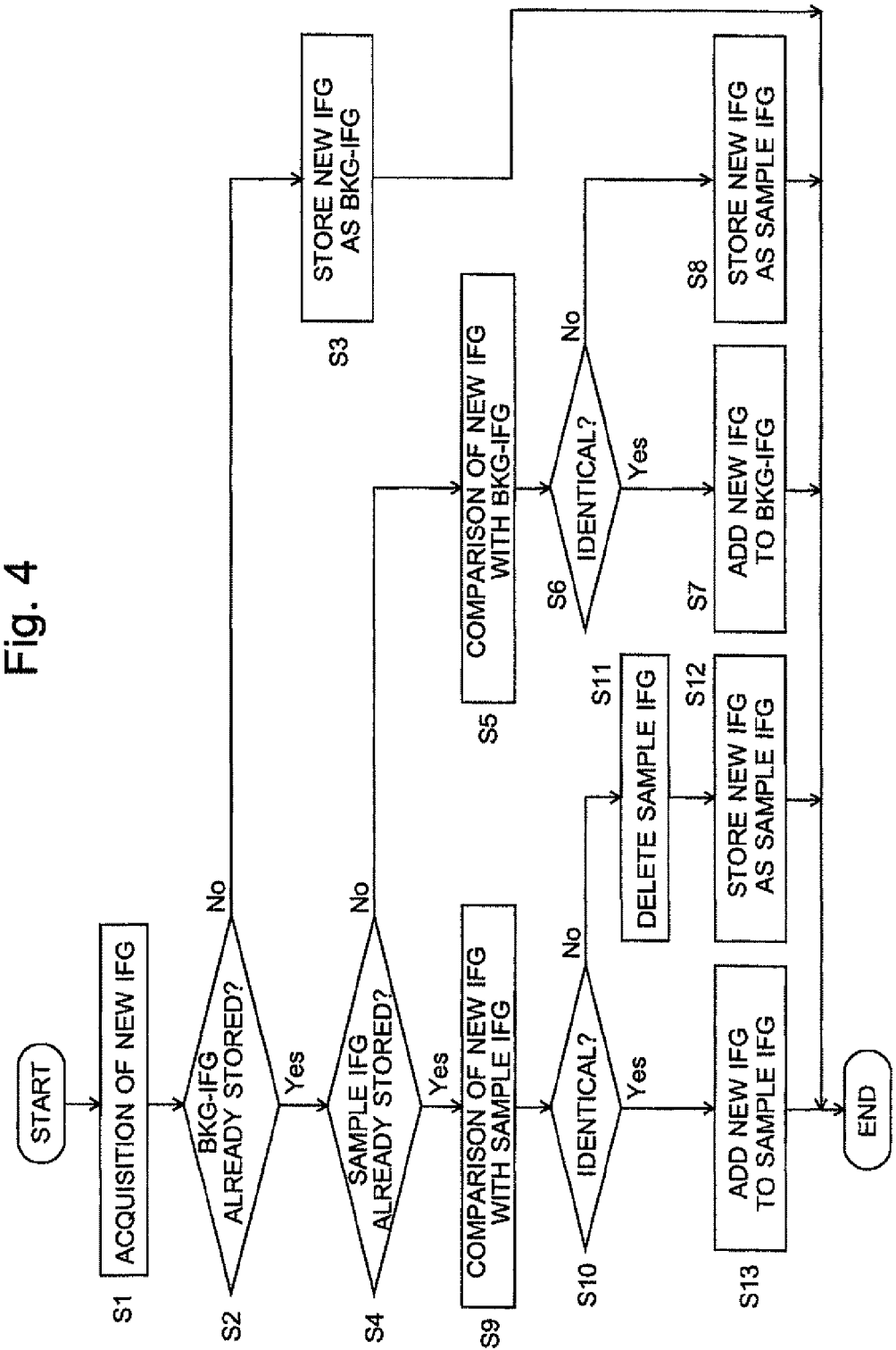
FIG. 4 is a flowchart showing the measurement control process in the FTIR of the present embodiment.

FIG. 4 is a flowchart showing the steps of a characteristic data processing operation in the FTIR of the present embodiment, and FIG. 3 is a graph showing one example of the interference-waveform data obtained in the FTIR of the present embodiment. Following FIG. 4, the characteristic data processing operation in the FTIR of the present embodiment and the thereby realized characteristic measurement operation are hereinafter described.

Initially, an operator powers on both the main unit 1 and the PC 3. Then, the control software on the PC 3 begins to operate, and the main unit 1 performs initial setting operations, such as a self diagnosis. The data processor 30 and the controller 40 in the PC 3 also perform initial settings, whereby the memories 32-34 are cleared. After the initial setting operations are completed, the infrared light source 11 is turned on under the control of the controller 40. Thus, an interfering light begins to enter the sample chamber 21. At this point in time, no sample 22 is set in the sample chamber 21. Therefore, an interference-waveform data with no sample is sent from the main unit 1 to the data processor 30. The data processor 30 stores the sequentially inputted data in the new IFG temporary memory 30. Meanwhile, the moving mirror 16 is repeatedly and reciprocally moved at a predetermined speed, and a new interferogram is acquired for each cycle of this reciprocal motion.

In the data processor 30, when a new interferogram (new IFG) is acquired (Step S1), the new IFG determination processor 36 determines whether a background interferogram (BKG-IFG) has already been stored in the BKG-IFG accumulation memory 34 (Step S2). Immediately after completion of the initial settings; no background interferogram is stored in the BKG-IFG accumulation memory 34. Accordingly, the operation proceeds from Step S2 to S3, and the RAN controller 35 moves the new interferogram from the new IFG temporary memory 32 to the BKG-IFG accumulation memory 34, and the process is completed.

When a new interferogram is acquired next time, the result of determination in Step S2 will be "Yes", and the new IFG determination processor 36 determines whether a sample interferogram (sample IFG) has already been stored in the sample IFG accumulation memory 33 (Step S4). Immediately after completion of the initial settings, no sample interferogram is stored in the sample IFG accumulation memory 33. Accordingly, the operation proceeds from Step S4 to S5, and the new IFG determination processor 35 compares the new interferogram with the latest background interferogram stored in the BKG-IFG accumulation memory 34.

For example, the two interferograms are compared as follows: Among a large number of data points (which may amount to 10,000 points) collected for each interferogram, 30 data points are selected from each side of the central point (the point where the time is 0), as shown in FIG. 3. Then, the difference in the data value between the two interferograms is calculated for each point, and the sum of these differences is calculated. If this sum is within a predetermined threshold range, the two interferograms are considered to be identical.

If the two interferograms are identical to each other ("Yes" in Step S6), the R/W controller 35 adds the new interferogram as one of the background interferograms to the BKG-IFG accumulation memory 34 (Step S7). If n sets of interferogram data have already been stored in this memory, the oldest set of data is discarded for the new set of interferogram data. Thus, the latest n sets of data are always held in the BKG-IFG accumulation memory 34. Generally, after the system is powered on, the background interferogram gradually shifts until the internal temperature of the system becomes stable. However, this shift is so slow that the result of determination in Step S6 will be positive. Accordingly, during this period of time, Step S6 is normally followed by Step S7 and the process on the new interferogram for one cycle is completed.

Until a sample 22 is set in the sample chamber 21 by the operator, the previously described processes of Steps S1, S2, S4, S5, S6 and S7 are sequentially performed, and the background interferograms stored in the BKG-IFG accumulation memory 34 are repeatedly updated. This means that a background measurement is automatically performed even though no explicit command for initiating the background measurement is entered through the operation unit 41. Since the latest n sets of background interferogram data are always stored in the previously described manner, it is possible to obtain a set of data that corresponds to the background measurement performed under sufficiently stable conditions, such as the internal temperature of the system. This is effective for enhancing the correctness and reliability of the data obtained by accumulation.

After the operator sets the prepared sample 22 at a designated position in the sample chamber 21, the interfering light thrown into the sample chamber 21 passes through the sample 22 before it reaches the infrared photodetector 24. When passing through the sample 22, the interfering light undergoes absorption by the sample 22. As a result, the form of the interference wave significantly changes from the form observed before the sample 22 was set. When no sample interferogram is stored in the sample IFG accumulation memory 33 and a new interferogram is acquired immediately after the sample is set, the operation proceeds from Step S4 through S5 to S6. This time, the result of determination in Step S6 will be negative. Upon receiving this result, the R/W controller 35 stores the new interferogram as a sample interferogram in the sample IFG accumulation memory 33 (Step S8), and the process is completed.

After the sample interferogram is stored in the sample IFG accumulation memory 33, when a new interferogram is acquired next time, the result of determination in Step S4 will be "Yes." Accordingly, the new IFG determination processor 36 compares the new interferogram with the latest sample interferogram stored in the sample IFG accumulation memory 33 (Step S9). The method for comparing the two interferograms may be the same as, or different from, the previously described method for comparing the new interferogram and the background interferogram. It is possible to use the same number of data points as mentioned earlier and only change the threshold range for checking the sum of the differences in the data values.

Immediately after the sample 22 is set in the sample chamber 21, the interferogram data is likely to be unstable due to a fluctuation of the ambience within the sample chamber or for other reasons. When a new interferogram is acquired during such an unstable phase of the interferogram data, the operation proceeds from Step S2 through S4 to S9, and the result of determination in Step S10 will be negative. Then, the sample interferogram stored in the sample IFG accumulation memory 33 is deleted (Step S11), in place of which the new interferogram is stored in the sample IFG accumulation memory 33 (Step S12).

Accordingly, after the sample 22 is set, no sample interferogram will be saved in the sample IFG accumulation memory 33 until the ambience and other conditions in the sample chamber 21 become stable. This means that the sample measurement is not actually performed until then. After the ambience in the sample chamber 21 and other conditions become stable and the detection signal produced by the infrared photodetector 24 is also stabilized, the new interferogram will be considered to be identical to the sample interferogram. In this case, the operation proceeds from Step S9 through S10 to S13, and the R/W controller 35 adds the new interferogram as one of the sample interferograms to the sample IFG accumulation memory 33 (Step S13).

After the sample 22 is set in the sample chamber 21, when n pieces of sample interferograms have been stored in the sample IFG accumulation memory 33, the measurement for the sample can be completed. After that, the n pieces of sample interferograms are read from the sample IFG accumulation memory 33 and sent to the accumulation processor 37 for accumulation. Similarly, the n pieces of background interferograms are read from the BKG-IFG accumulation memory 34 and sent to the accumulation processor 37 for accumulation. The two interferograms obtained by accumulation are respectively subjected to Fourier transformation to obtain an absorption spectrum and a background spectrum. Then, the background spectrum is subtracted from the absorption spectrum to obtain a spectrum that includes no background influences and correctly reflects the absorption due to only the sample 22.

As described thus far, the FTIR of the present embodiment automatically begins to collect background interferogram data when an operator powers on the system. Furthermore, it begins to collect sample interferogram data when the operator sets a sample 22 in the sample chamber 21. Since these data-collecting processes do not require any key operation to be performed on the operation unit 41 of the PC 3, the operator does not need to go to the PC 3 after setting the sample 22. Furthermore, no background measurement needs to be intentionally conducted by the operator since the system can automatically collect accurate background interferogram data.

In the previous embodiment, the method for comparing a new interferogram with either a background interferogram or a sample interferogram to determine whether or not the compared interferograms are identical, i.e. the method for determining the degree of the temporal change in the detection data, is not limited to the previously described method.

The previous embodiment was an example in which the present invention was applied to an FTIR spectrophotometer. It is also possible to apply the present invention to other types of spectrophotometers, such as a single-beam ultraviolet-visible spectrophotometer.

It is evident that any change, modification or addition appropriately made within the spirit of the present invention for other aspects of the system will fall within the scope of claims of this patent application.

The invention claimed is:

1. A spectrophotometer for throwing measurement light onto a sample, for detecting transmitted light from the sample by means of a detector, and for obtaining information relating to absorption of light at a specific wavelength by the sample based on detection data, comprising:
   a) a recognizing means for obtaining the detection data continuously or at predetermined intervals of time, and for recognizing that a sample to be analyzed is set in an optical path judging from a degree of a temporal change in the detection data; and
   b) a processing means for processing the detection data, wherein the processing means initiates, in response to a recognition by the recognizing means, a process in which the detection data is treated as measurement data for the sample, but the processing means performs a process in which the detection data is treated as background data with no sample while the detection data is obtained before the recognizing means recognizes a presence of the sample to be analyzed and the temporal change of the detection data is within a predetermined threshold range.

2. The spectrophotometer according to claim 1, wherein, after the processing means begins to treat the detection data as the measurement data in response to the recognition by the recognizing means, when newly obtained detection data is found to be significantly different from the measurement data, the processing means discards the measurement data.

3. The spectrophotometer according to claim 1, wherein:
   the spectrophotometer is a Fourier transform infrared spectrophotometer in which an interferogram whose amplitude temporally changes is used as the measurement light; and
   the recognizing means recognizes a presence of the sample to be analyzed from a temporal change in interference-waveform data obtained before Fourier transformation.

4. The spectrophotometer according to claim 3, wherein the processing means accumulates the measurement data and/or background data as interference-waveform data.

5. The spectrophotometer according to claim 2, wherein:
   the spectrophotometer is a Fourier transform infrared spectrophotometer in which an interferogram whose amplitude temporally changes is used as the measurement light; and
   the recognizing means recognizes a presence of the sample to be analyzed from a temporal change in interference-waveform data obtained before Fourier transformation.

6. The spectrophotometer according to claim 5, wherein the processing means accumulates the measurement data and/or background data as interference-waveform data.

* * * * *